United States Patent [19]

O'Gara

[11] Patent Number: 5,077,209

[45] Date of Patent: Dec. 31, 1991

[54] DICARBOXYLIC ACID TRANSPORT GENES

[75] Inventor: Fergal O'Gara, Bishopstown, Ireland

[73] Assignee: National Development Corporation, Dublin, Ireland

[21] Appl. No.: 224,609

[22] Filed: Jul. 27, 1988

Related U.S. Application Data

[63] Continuation-in-part of Ser. No. 889,779, Jul. 28, 1986, abandoned.

[30] Foreign Application Priority Data

Jul. 27, 1987 [CA] Canada ................................. 543043

[51] Int. Cl.$^5$ ..................... C12N 15/11; C12N 15/63; C12N 1/21; C07H 15/12
[52] U.S. Cl. .................................. 435/172.3; 536/27; 435/252.2; 435/252.3; 435/320.1; 935/42; 935/59
[58] Field of Search ............... 435/172.1, 172.3, 252.2, 435/252.3, 320; 935/42, 64; 536/27

[56] References Cited

FOREIGN PATENT DOCUMENTS

0164992A2 12/1985 European Pat. Off. .
0255340A1 2/1988 European Pat. Off. .

OTHER PUBLICATIONS

Ronson, Astwood & Dowine, Modecular Cloning and Genetic Organization of $C_4$-Dicarboxylate Transport Genes from *Rhizobium leguminosarum* (1984), J. Bacteriol. 160, 903-909.

Ronson, Lyttleton & Robertson, $C_4$-Dicarboxylate Transport Mutants of Rhizobium Trifolii Form Ineffective Nodules on Trifolium Repens (1981), PNAS (U.S.A.), 78, 4284-4288.

Finan, Wood & Jordan, Symbiotic Properties of $C_4$ dct Mutants, J. Bact. 154:1403-1413 (1983).

Ditta, Stanfield, Corbin & Helsinki, Broad Host-Range DNA Cloning System, PNAS 77:7347-7351 (1980).

*Primary Examiner*—Richard A. Schwartz
*Assistant Examiner*—Richard M. Lebovitz
*Attorney, Agent, or Firm*—Wegner, Cantor, Mueller & Player

[57] ABSTRACT

The invention relates to DNA fragments encoding genes which complement dicarboxylic acid transport mutants of Rhizobium species to plasmids encoding such DNA sequences and to bacterial hosts carrying the said plasmids. The invention further relates to a method of increasing dicarboxylic acid transport in Rhizobium species and to a method of increasing the nitrogen fixing ability of plants by infecting or inoculating the plants with bacterial hosts containing the above described DNA fragments.

13 Claims, 6 Drawing Sheets

DICARBOXYLIC ACID TRANSPORT GENES

This application is a continuation-in-part of U.S. Pat. application Ser. No. 889,779 filed 28th July 1986 now abandoned.

TECHNICAL FIELD

The present invention relates to the cloning of dicarboxylic acid transport (dct) genes, to DNA sequences encoding dicarboxylic acid transport genes and to the use of such DNA sequences in the improvement of bacterial strains capable of carrying out nitrogen fixation.

BACKGROUND TO THE INVENTION

The fixation of molecular nitrogen from the air, i.e. its reduction to yield ammonia and other biologically useful forms of nitrogen is an extremely important process in the biosphere. However, it can be carried out by only a limited number of organisms. The majority of organisms must obtain nitrogen in a combined form such as nitrate, ammonia or amino acids. Most leguminous plants e.g. clover and alfalfa can fix atmospheric nitrogen. but the process requires the symbiotic action of the host plant and bacteria present in the root nodules of the plant. The bacteria involved in nitrogen fixation belong mainly to the genus Rhizobium, and these bacteria enter the cortical parenchyma of the root where they give rise to nodules. The nodules are highly organized structures with membraneous sacks containing colonies of bacteria. Supplied with carbon compounds from photosynthesis by the plant, the bacteria fix nitrogen, producing ammonia which is provided to the plant for amino acid biosynthesis, thus aiding protein formation in the plant. Leguminous plants can therefore be grown without synthetic nitrogen fertilizers which represents a considerable financial saving for the farmer since it allows for protein production on a cost effective basis.

The process of nitrogen fixation is the basis for the use of clover and alfalfa in crop rotation, since the growth of such plants increases the utilizable nitrogen in the soil.

Legume seeds which have been coated with Rhzobium species are currently available commercially. This allows for the formation of nitrogen fixing root nodules to be formed as soon as the seeds germinate. The seeds are coated with naturally occurring strains which have been isolated from soil and selected for their efficiency in fixing nitrogen and their ability to compete with other bacterial strains in the soil.

Evidence indicates that the nitrogen-fixing capacity of the Rhizobiumlegume symbosis is influenced by the amount of photosynthate available to the bacteria in the root nodule (Hardy and Havelka, (1975) In: Nutman P.S. (ed) International biological programme : symbotic nitrogen fixation in plants. Cambridge University Press, New York, pp 421–439; Havelka and Hardy (1976) In : Newton W.E., Nyman. C.Y. (eds) Proceedings of the first international symposium on nitrogen fixation. Washington State University Press, Pullman, Washington. pp 456–475; and Ryle et al (1979) J. Exp. Bot. 30 : 135–144). It is widely thought that one of the key limiting steps in symbiotic nitrogen-fixation is the availability of the carbon (i.e. energy) source made available to the bacteria.

The inventors of the present invention do not agree fully with this hypothesis but believe that the limiting factor may not be the availability of a carbon source but rather the transport of the carbon source into the bacteria in the root nodule.

Tricarboxylic acid (TCA) cycle intermediates have been implicated as the major carbon source supplied to bacteroids (i.e. the differentiated form of bacteria which fixes nitrogen in the root nodule) in pea and clover symbiosis. The evidence for this is based on the fact that dicarboxylic acid transport mutants of *Rhizobium leguminosarum* (Finan et al (1983) J. Bacteriol 148, 193–202; Glenn and Brewin (1981) J. Gen. Microbiol. 126, 237–242) and *R. Trifolii* (Ronson et al (1981) PNAS (USA) 78, 4284–4288) form ineffective nodules despite being able to utilize other carbon sources. In *R. meliloti*, a functional TCA cycle is necessary to support nitrogen-fixation in the bacteroid as shown by the fact that mutants defective in succinate dehydrogenase (Gardiol et al (1982) J. Bacteriol. 151 1621–1623) and alpha-ketoglutarate dehydrogenase (Duncan and Fraenkel (1979) J. Bacteriol. 37 415–419) form ineffective nodules.

Dicarboxylic acid transport genes from *R. leguminosarum* have been isolated (Ronson et. al. (1984) J. Bacteriol. 160 903–909) but they did not lead to a significant effect on the symbiotic response of the wild-type strain.

The strain formerly known as *Rhizobium japonicum* has been officially re-classified as *Bradyrhizobium japonicum* and references to that strain in this specification have been amended accordingly. The term "Rhizobium species" as used herein includes both Rhizobium and bradyrhizobium species.

OBJECTS OF THE INVENTION

It is an object of this invention to increase the nitrogen fixing ability of leguminous plants.

SUMMARY OF THE INVENTION

The present invention relates to a biologically pure fragment of DNA encoding genes which complement dicarboxylic acid transport mutants of Rhizobium species, particularly fragments of DNA isolated from *R. meliloti*. IN particular the invention relates to fragments of DNA which confer increased nitrogen fixing ability on plants infected/inoculated with Rhizobium species.

The invention also relates to plasmics carrying a DNA fragment encoding genes which complement the dicarboxylic acid transport mutants of Rhizobium species, more particularly such as DNA fragment contained in plasmid 4:46 described herein, or a DNA fragment substantially similar thereto.

In particular, the invention relates to plasmids deposited with the National Collection of Industrial Bacteria Torry Research Station, Aberdeen, Scotland, on 22nd July 1986, under the accession numbers NCIB 12293. NCIB 12294 and NCIB 12295.

The invention further relates to isogenic derivatives of the plasmids deposited under accession Nos. NCIB 12293, NCIB 12294 and NCIB 12295, plasmids which are substantially similar thereto in the region of DNA encoding genes which complement dicarboxylic acid transport mutants of Rhizobium species, particularly plasmids having at least 80% homology with the said DNA region; and to DNA in such plasmids encoding genes which complement dicarboxylic acid transport mutants of Rhizobium species.

The invention also relates to bacterial hosts containing one or more of the plasmids as defined above. In particular, the invention provides bacterial hosts containing plasmids having the accession numbers NCIB 12293, NCIB 12294 and NCIB 12295.

The invention especially relates to all of the above-defined materials in biologically pure form.

The invention also provides a method of increasing dicarboxylic acid transport in Rhizobium species by transferring into the said species a DNA fragment encoding genes which complement dicarboxylic acid transport mutants of Rhizobium species, or a plasmid carrying such a DNA fragment.

The invention further provides a method of increasing the nitrogen fixing ability of plants by transferring into the plants a DNA fragment encoding genes which complement the dicarboxylic acid transport mutants of Rhizobium species or by infecting/inoculating the said plants with a bacterial host carrying a DNA fragment encoding genes which complement the dicarboxylic acid transport mutants of Rhizobium species, or a bacterial host transformed with a plasmid carrying such a DNA fragment.

In a still further aspect of the invention there are provided seeds of plants which have been coated with bacterial hosts as defined above.

It could not be predicted that the isolation of DNA fragments which complement dct mutants of Rhizobium species and their insertion into Rhizobium species or plants would lead to increased dicarboxylic acid transport which could lead to increased nitrogen fixing ability in Rhizobium species or plants.

DETAILED DESCRIPTION OF THE DRAWINGS

DETAILED DESCRIPTION OF THE INVENTION

ISOLATION OF DCT MUTANTS OF R. MELILOTI

Chemical (NTG and Mitomycin C) and transposon (Tn 5) mutagenesis was employed to generate mutants of Rhizobium meliloti which are defective in succinate utilization.

Transposon Tn5 mutaqenesis. Tn5 was introduced into R. meliloti CM2 using the Tn5-Mob suicide vector system developed by Simon et al. (1983 Biotechnol. 1 784–791). Tn5 exconjugants were selected on MSY (mannitol/salts/yeast) medium containing neomycin (100 μg/ml).

NTG mutaqenesis. Late log phase R. meliloti CM2 cultures grown in MSY were treated with N-methyl-N-nitro-N-nitrosoguanidine (NTG) 300 μg/ml for 90 min. at 30° C. The mutagen was removed by pelleting cells and washing twice in saline buffer. Cells were resuspended in MSY and incubated for 6–8 h to allow mutant segregation and subsequently recovered on appropriate selective media.

Mitomycin C mutaqenesis. Mitomycin C (20 μg/ml) was added to a freshly inoculated R. meliloti CM2 culture in MSY and incubated for 36 h. The mutagen was removed and cells treated as for the NTG mutagenesis.

Mutant isolation. Mutants defective in the utilization of dicarboxylic acids were isolated by screening mutagenised cultures for clones unable to grow on succinate-$NH^+$ or which appeared white on succinate-glucose-$NH^+$ tetrazolium plates (Manian et al. (1982) Arch. Microbiol. 133 312–317).

R. meliloti CM2 exconjugants containing Tn5 were obtained at a frequency of $6.4 \times 10^{-5}$. These exconjugants yielded a wide variety of mutants impaired in carbon metabolism. From a total of 1,555 mutants screened, only one defective in succinate metabolism was isolated (R. meliloti CM20). NTG mutagenesis of R. meliloti CM2 also induced mutants defective in carbon metabolism and a number of mutants specifically defective in succinate utilization were isolated. No mutants defective in succinate utilization were recovered using mitomycin C treatment.

From this group of mutants unable to grow on succinate, those which were specifically defective in the transport of dicarboxylic acids were identified by checking the growth patterns of a range of different carbon substrates (Table 1). Failure of a mutant to utilize succinate, malate and fumarate was taken as an initial indication of a defect in the dicarboxylic acid transport system as all three dicarboxylic acids are known to share a common transport system in other bacteria. In addition the ability of these mutants to grow on arabinose indicates the presence of a functional TCA cycle (Duncan and Fraenkel (1979) J. Bacteriol. 37 415–419).

TABLE 1

| | | Mutant Mutagen Growth on | | | | |
|---|---|---|---|---|---|---|
| | | Succ | Mal | Fum | Glut | Ara |
| Rhizobium meliloti | | | | | | |
| CM10 | NTG | + | + | + | +++ | +++ |
| CM11 | NTG | − | − | − | +++ | +++ |
| CM12 | NTG | − | − | − | +++ | +++ |
| CM13 | NTG | − | − | − | +++ | +++ |
| CM14 | NTG | − | − | − | +++ | +++ |
| CM15 | NTG | − | − | − | + | +++ |
| CM16 | NTG | + | + | + | +++ | +++ |
| CM17 | NTG | − | − | − | +++ | +++ |
| CM18 | NTG | − | − | − | +++ | +++ |
| CM19 | NTG | − | − | − | ++ | +++ |
| CM20 | Tn5 | − | − | − | +++ | +++ |
| CM2 | — | +++ | +++ | +++ | +++ | +++ |

TABLE 1. Growth properties of Rhizobium meliloti CM2 mutants unable to grow on succinate. Mutants unable to grow on succinate (0.1% w/v) minimal medium were examined for growth on minimal media containing a single carbon source, i.e. malate (0.1% w/v), fumarate (0.1% w/v), glutamate (0.1% w/v) or arabinose (0.1% w/v). Growth was determined by measuring the optical density of the culture at 420 nm at 30°

C. over 72 h period, and scored as follows: (+++=complete growth; ++=fair growth; +=no growth). The doubling time for R. meliloti CM2 grown on succinate-NH+ medium at 30° C. is 3.7 h.

Succinate Uptake Assay.

Figure 1:
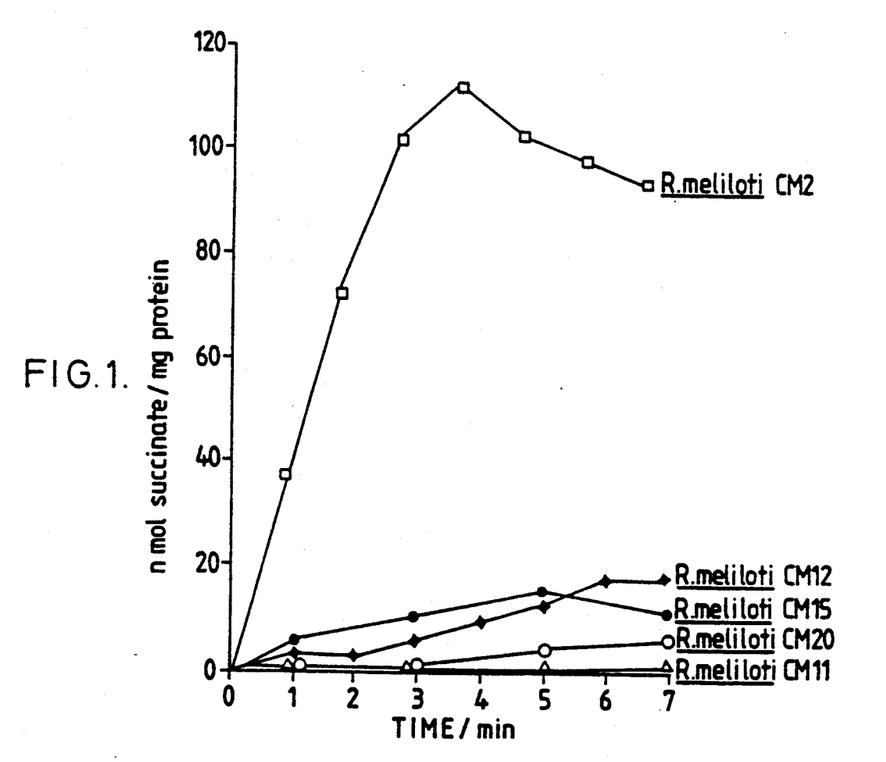
FIG. 1 is a graph showing succinate uptake by both wild-type and mutant strains of R. meliloti CM2.

The mutants unable to grow on TCA cycle intermediates were then examined for their ability to transport $^{14}C$ labelled succinate (FIG. 1). Succinate uptake analysis was carried out in minimal Rhizobium salts (O'Gara and Shanmugam (1976) Biochem. Biophys. Acta. 500 277-290) buffer containing 50 mM 3-N-morpholino propane sulfonic acid (MOPS) (sodium salt pH 7.0) with the specified carbon source. A mid log phase culture was harvested, washed twice in and resuspended in minimal salts buffer to give a final protein concentration of 1.5-2 mg/ml. The transport assay was a modification of the procedure of Finan et al. ((1981) J. Bacteriol. 148 193-202 ). For transport assays the minimal salts buffer (2 ml) contained (1,4-$^{14}C$) succinate (22 $\mu M$;118 mCi/mmol specific activity) in the presence of 8 mM unlabelled succinate and 1 ml of cells. Aliquots (100 $\mu l$) of the cel suspension were removed at 1 min intervals, filtered. (0.45$\mu$ cellulose nitrate filters) washed twice in minimal salts buffer (3 ml) and added to scintillation fluid 4 g 2-5-diphenyloxazole (PPO). 0.3 g 1,4-bis (2-5-phenloxazolyl) benzene (POPOP) in 660 ml toluene made up to 1l with Triton X-100. The samples were counted in a Beckman LS 7.000 microprocessor scintillation counter.

This uptake analysis shows that both NTG mutants (R. meliloti CM10-19) and the Tn5 mutant (R. meliloti CM20) are unable to accumulate $^{14}C$-labelled succinate indicating a defect in their dicarboxylic acid transport system. The ten NTG mutants were obtained from two different mutant pots and therefore siblings may be present in the R. meliloti CM10-CM16 and R. meliloti CM17-19 subgroups. Reversion analysis was carried out on five of the dct mutants (R. meliloti ; CM10, CM11. CM12, CM16 and CM20). The mutants were reverted on malate and their growth characteristics examined on other dicarboxylic acids. All mutants tested could be reverted at a high frequency (Table 2) and they also regained the ability to grow on fumarate and succinate as the sole carbon source. A similar result was also obtained when succinate was used for reversion tests.

TABLE 2

| Revertant | Reversion | Reversion medium | Growth on frequency | | |
|---|---|---|---|---|---|
| | | | Succ | Fum | Mal |
| Rhizobium meliloti | | | | | |
| CM11.1 | Malate | $8.2 \times 10^{-6}$ | +++ | +++ | +++ |
| CM10.1 | NH4 | $4.4 \times 10^{-5}$ | +++ | +++ | +++ |
| CM16.1 | | $6.1 \times 10^{-6}$ | +++ | +++ | +++ |
| CM12.1 | | $7.3 \times 10^{-5}$ | +++ | +++ | +++ |
| CM20.1 | | $1.8 \times 10^{-5}$ | +++ | +++ | +++ |

TABLE 2: Reversion frequency and growth response of R. meliloti dct mutants. R. meliloti dct mutants were reverted on the dicarboxylic acid malate (0.1% w/v). Reversion frequency was determined by dividing the number of revertants obtained by the total number of cells plated as determined by a dilution series of cell suspension plated on MSY media. The revertants were subsequently grown on minimal media plates containing the other dicarboxylic acids as sole carbon sources at 30° C. for 72-96 h; +++=complete growth.

Both the high reversion frequency and the revertant phenotype suggested that a point mutation was responsible for the defect in dct transport in each case. Reversion analysis on R. meliloti CM20 showed that while growth on succinate was restored, the Tn5 encoded neomycin/kanamycin resistance was maintained. This suggested that the transposon had either transposed to a new site in the R. meliloti genome or that the original mutation was not induced by Tn5.

Verification of the Tn5 associated nature of the mutation was obtained using coinheritance studies during gene transfer experiments with the wild type strain. The R68 derived plasmid pJB3J1 kanamycin sensitive (Kan$^s$) (Brewin et al. (1980) J. Gen. Microbiol. 120 413-420) capable of promoting chromosome transfer in R. meliloti (Kondorsoi et al. (1977) Nature 268 525-527) was conjugated into R. meliloti CM20 on MSY media at 30° C. for 24 h. R. meliloti CM20 pJB3J1 exconjugants were selected on MSY Rif Tc plates. pJB3J1 was subsequently transferred from R. meliloti CM20 to the wild type R. meliloti strain. Tn5 containing exconjugants were selected on MSY Kan and subsequently the succinate phenotype was checked on minimal medium containing succinate (0.1%).

Using this system 100% cotransfer of the Tn5 encoded antibiotic resistances and the succinate minus phenotype (approximately 20 clones) was observed in conjugation experiments into the wild type R. meliloti strain. This indicates that the succinate minus phenotype R. meliloti CM20 was Tn5 induced.

SYMBIOTIC PROPERTIES

Alfalfa plants were inoculated with the dct mutants of R. meliloti CM2. These mutant strains nodulated Alfalfa plants, however, the nodules were small and white compared to the larger pink nodules observed on the R. meliloti CM2 control plants. When tested for N$_2$-fixation ability as assayed by acetylene reduction, the mutants only showed 10-50% of the wild type activity (Table 3). Revertants of both NTG and Tn5 dct mutants all fixed N$_2$ at rates similar to R. meliloti CM2 indicating the failure of these mutants to promote N$_2$-fixation was directly due to their inability to transport TCA cycle intermediates. This suggests that dicarboxylic acids constitute an important component of the photosynthate partitioned to be bacteriod during N$_2$ fixation in the R. meliloti-Alfalfa symbiosis.

TABLE 3

| Strain | dct Phenotype | Nodulation | N$_2$-fixation nmol C$_2$H$_4$/min · g nodule weight |
|---|---|---|---|
| Rhizobium meliloti | | | |
| CM2 | + | + | 11.6 |
| CM10 | − | +· | 5.9 |
| CM11 | − | + | 0.82 |
| CM12 | − | + | 0 |
| CM13 | − | + | 0.9 |
| CM14 | − | + | 0 |
| CM15 | − | + | 0 |
| CM16 | − | + | 0.14 |
| CM20 | − | + | 2.24 |
| CM20.1 | + | + | 11.1 |
| CM20.2 | + | + | 10.8 |
| CM11.1 | + | + | 11.8 |
| CM10.1 | + | + | 11.4 |

TABLE 3. Symbiotic properties of dct mutants and their revertants. Wild type dct mutant and revertant strains of R. meliloti were inoculated onto Alfalfa plants and assayed for nitrogenase activity after 7 weeks growth.

Nitrogenase activity in nodules

Alfalfa seeds were surface sterilized using 70% ethanol and 7% calcium hypochloride and water washes. Sterilized seeds were germinated in large test tubes containing vermiculite in the dark. The plants were inoculated with the appropriate *R. meliloti* strain which had been resuspended in Rhizobium salts medium containing no carbon or nitrogen source. After 7 weeks in a growth room plants were harvested, nodules picked off and nitrogenase activity determined by the acetylene reduction technique as previously described (O'-Gara and Shanmugam (1977) Biochem. Biophys Acta 437 313–327).

CLONING OF DCT GENES IN *R. MELILOTI*

Mutants unable to transport succinate were used to isolate dct genes from a *R. meliloti* gene bank.

Cloning of succinate uptake genes.

Succinate transport genes of *R. meliloti* were cloned using a complementation approach with recombinant plasmids from a *R. meliloti* gene bank carrying segments of *R. meliloti* F34 total DNA cloned in pRK290 (Ditta et al. (1980) PNAS (USA) 77 7347–7351). obtained from G. Ditta and D. Helsinki, University of California, San Diego. Individual clones from the gene bank were mated with *R. meliloti* CM2 dct mutants in the presence of the mobilizing plasmid pRK2013. Matings were carried out on MSY plates at 30° C. for 36–48 h. ExconJugants were isolated on MSY containing 5 µg/ml tetracycline to select for transfer of the gene bank clones into *R. meliloti* strains. These exconjugants were then replica plated onto minimal medium plates containing succinate (0.1%) and $(NH_2)_2SO_4$. Clones growing on minimal medium with succinate as the sole carbon source had obtained complementing DNA from the *R. meliloti* F34 gene bank. Plasmid DNA for restriction analysis was obtained from the corresponding HBIOI pRK290 gene bank clones. The pRK290 gene bank of *R. meliloti* F34 yielded clones capable of complementing two of the dct mutants (*R. meliloti* CM10 and CM12). Both of these mutants were found to be complemented by the same two clones from the gene bank.

Plasmid DNA isolation and restriction.

Plasmid DNA was isolated from HBIOI using both rapid and large scale isolation techniques. The rapid procedure (Birnboim and Doly (1979) Nucl. Acids Res. 7 1515–1513) was carried out on cultures (10 ml) grown overnight at 37° C. in LB medium containing tetracycline (5/µg/ml). Large scale DNA preparation was carried out using the cleared lystate technique followed by ethidium bromide-cesium chloride equilibrium centrifugation. (Clewell and Helsinki (1969) PNAS (USA) 62 1159–1166). Restriction endonuclease enzymes [Boehringer (BCL)] were used according to the manufacturers specifications. Analysis of restriction fragments was performed by standard agarose gel electrophoresis (1% agarose, 89 mM Tris, 85 mM Boric acid, 2.5 mM EDTA pH 8.0) and ethidium bromide staining (Maniatis et al. (1982) Cold Spring Harbor Laboratory, New York).

Figure 2:
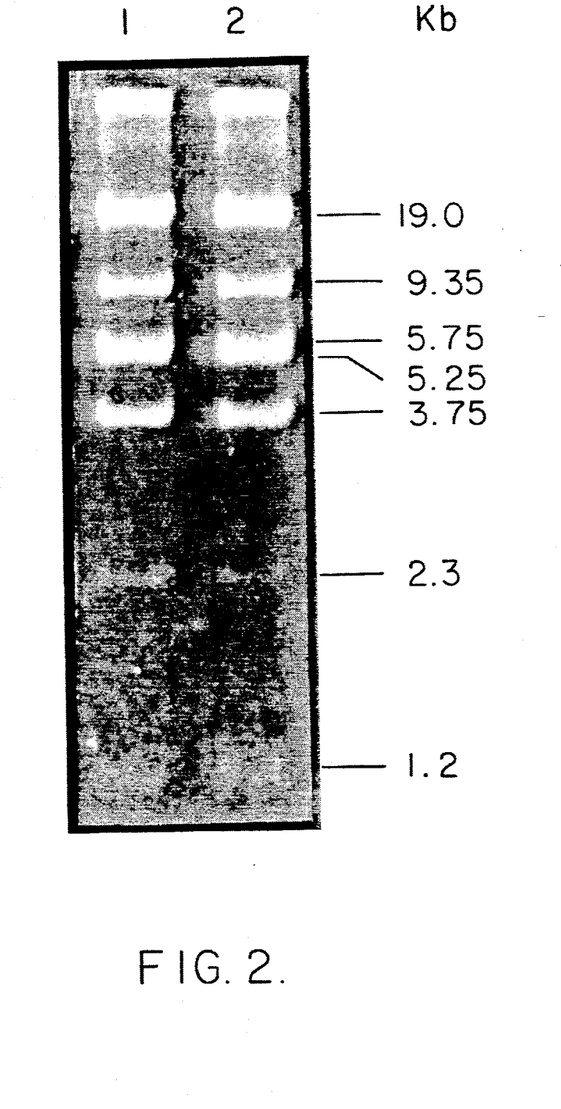
FIG. 2 shows an analysis of pRK 290: 4:46 and pRK 290:5:11 by agarose gel electrophoresis. Track 1 :-pRK 290:4:46 Bgl II, Eco RI. Track 2:-pRK 290:5:11 Bgl II, Eco R1.

Restriction analysis of the plasmids from these two clones indicated that both contained the same *R. meliloti* F34 DNA insert (FIG. 2. track 1 and 2). These plasmids (pRK290:4:46 and pRK290:5:11) contained a 40 Kb DNA insert consisting of five BqlII fragments (16.6, 8.7, 7.6. 5.9 and 1.2 Kb in size) These plasmids contain 7 BamHI sites (fragment sizes are 25.58, 14.15, 7.9, 4.55, 3.55, 2.9 and 1.1 Kb), 4 ClaI sites (fragment sizes are 36.4, 13.4. 6.7 and 3.45 Kb) and 7 EcoRI sites (fragment sizes are 21.55, 12.45, 6.15, 5.50, 3.20, 1.55 and 1.45 Kb). In addition there are also multiple sites for HindIII. PstI, PvuII and SmaI. None of the remaining nine succinate transport mutants were complemented by pRK290:4:46 or the pRK290 based BqlII gene bank. The inability to complement the remaining succinate uptake mutants indicates the involvement of further gene cluster(s) in dicarboxylic acid transport in *R. meliloti* which are not present or functional on the pRK290:4:46 fragment or in the pRK290 BglII gene bank.

EFFECT OF DCT GENE DOSAGE ON SUCCINATE TRANSPORT IN *R. MELILOTI*

The cloned DNA insert in plasmid pRK290 encoding succinate transport gene(s) was exploited to create a *R. meliloti* strain with an increased copy number of the succinate transport genetic components. This strain was then used to investigate the effect of increased gene dosage on succinate transport. Plasmid pRK290:4:46 which has a copy number of 4–5 was used to transfer the cloned transport component(s) into the wild type strain *R. meliloti* CM2. Rates of $^{14}C$ labelled succinate uptake were compared in *R. meliloti* CM2 and *R. meliloti* CM2 (pRK290:4:46) grown in succinate-NH. minimal medium. The uptake rate measured over a seven-minute period was twofold higher in the strain harbouring plasmid pRK290:4:46 (78 nmol/mg protein min) compared to the wild type strain (42 nmol/mg protein min). These results indicate the succinate uptake rates in *R. meliloti* can be enhanced by increasing the gene dosage of specific determinant(s) associated with the 40.0 Kb DNA insert in plasmid pRK290:4:46.

IDENTIFICATION OF PLASMIDS 4:46 AND MC5 CONTAINING DCT GENES

Plasmid 4:46

*R. meliloti* CM12 was complemented using the pRK290 BglII gene bank of *R. meliloti* F34 contained in *E. coli* HBIOI (obtained from Prof. D.R. Helsinki of the University of California at San Diego). This gene bank is maintained on 28 LB plates containing 10 µg/ml of Tc with 49 clones per plate.

*R. meliloti* CM12 was grown in 50 mls of MSY while the mobilizing strain pRK2013 required to mobilize pRK290 was grown in 50 ml of LB broth containing 25 µg/ml of Kan to maintain pRK2013.

The HBIOI *R. meliloti* F34 gene bank containing the 2013 mobilizing plasmid was mated with *R. meliloti* CM12 on MSY plates for 48 hours at 30° C. The mating mix was then transferred to exconjugant selection plates, i.e., MSY rif Tc (100 µg/ml rif selecting for the mutant strain while 5 µg/ml Tc selects for pRK290 plasmid transfer) and incubated at 30° C. for up to 5 days. Exconjugants were then transferred to succinate NH4 selective plates. Clones which grew on these plates presumably obtained complementing DNA from the gene bank. Plasmid DNA for study was obtained from the corresponding HB101 gene bank clones on LB Tc plates. The complementing plasmid is referred to as 4:46. A flow diagram of the complementation procedure is as follows:

Flow diagram of Complementation Procedure 50 mls of an overnight 2013 culture grown in LB$_{Kan}$ (25 μg/ml) centrifuged at 7,000 rpm for 5 min at 4° C.

↓

2013 pellet resuspended in 3 ml of ringers and LB plates spread with 0.1 ml.

↓

HB101 pRK290 gene bank transferred to seeded plates and incubated overnight at 37° C.

↓

Exconjugants selected on LB$_{Tc\ Kan}$

↓

50 ml of a 24 hr, mutant culture centrifuged at 7,000 rpm for 5 mins, at 4° C. Pellet washed in ringers and recentrifuged.

↓

Mutant pellet resuspended in 3 ml of ringers and MSY plates spread with 0.1 ml.

↓

Gene bank with 2013 transferred onto seeded MSY plates and incubated at 30° C. for 48 hours.

↓

Mating transferred to MSY rif Tc to select exconjugants and incubated at 30° C. for 4–5 days.

↓

Exconjugants transferred to Suc NH$_4$ plates and incubated at 30°C. for 4–5 days.

↓

Suc NH$_4$ plates examined for complemented mutant growth.

↓

Corresponding gene bank clone used for plasmid isolation.

R. meliloti CM12 containing plasmid 4:46 was deposited with the National Collection of Industrial Bacteria, Torry Research Station, Aberdeen, Scotland under the accession number 12294. Plasmid MC5

Plasmid MC5 was identified by an essentially similar procedure to the one described above except that a pLAFRI gene bank of R. meliloti F34 (also obtained form Prof. D.R. Helsinki) was used as the source of the complementing plasmids.

R. melilloti CM12 containing plasmid MC5 was deposited with the National Collection of Industrial Bacteria, Torry Research Station, Aberdeen, Scotland under the accession number 12293.

Analysis of Plasmids 4:46 and MC5

Figure 3:
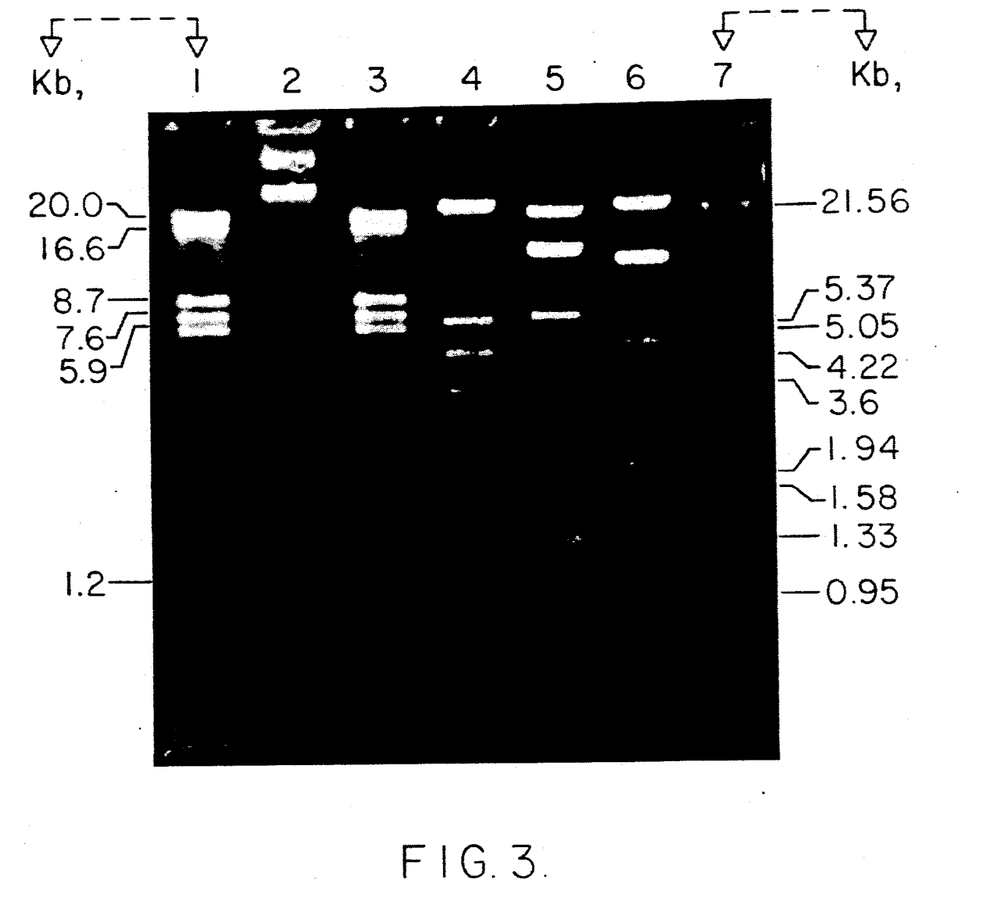
FIG. 3 shows an analysis of plasmid 4:46 by agarose gel electrophoresis. Track 1:- BolII, Track 2: SalI. Track 3 :-BqlII/SalI, Track 4:-PstI, Track 5:- ClaI, Track 6:- HindIII.
Figure 4:
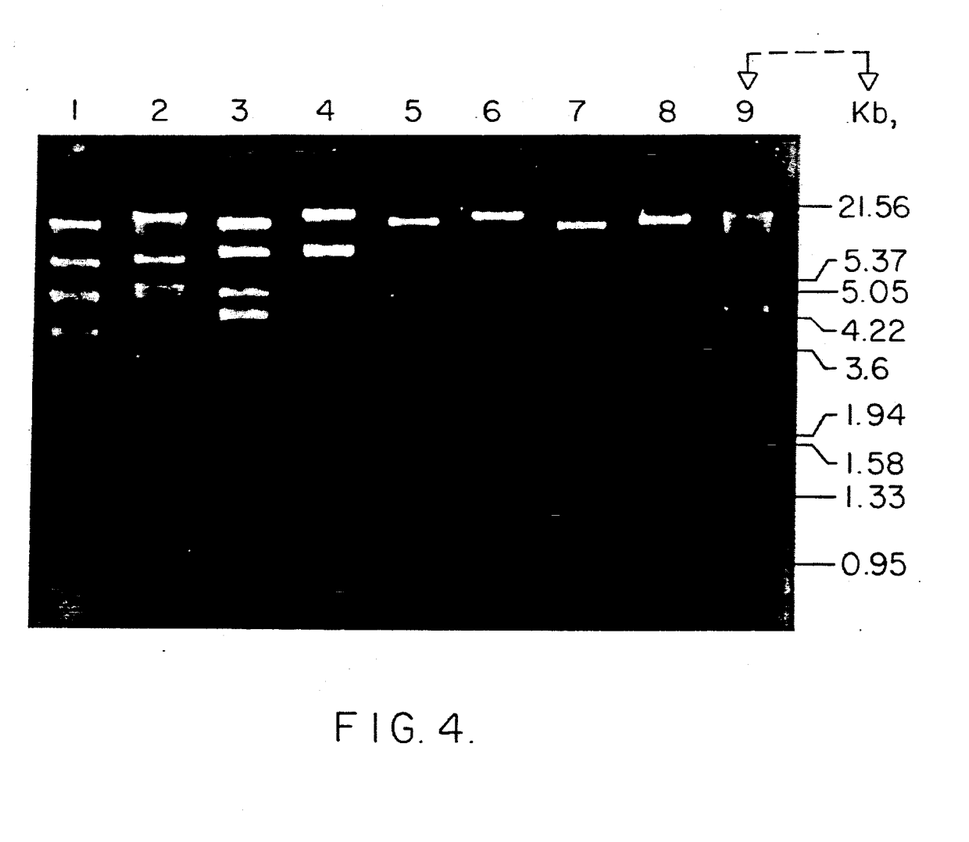
FIG. 4 shows an analysis of plasmid 4:46 by agarose gel electrophoresis. Track 1:- BolII EcoRI. Track 2:- Eco RI, Track 3:-BqlII/HindII, Track 4:-HindIII, Track 5:- BqlII/PstI, Track 6:-PstI, Track 7:-BolII/SmaI, Track 8:-SmaI.

An analysis of plasmids 4:46 and MC5 was carried out using a variety of restriction enzymes. The restriction data is as follows and as shown in FIGS. 3 and 4:

| Restriction Enzyme | No. of Fragments |
|---|---|
| Plasmid 4:46 | |
| BglII | 6 |
| ClaI | 4 |
| EcoRI | 7 |
| HindIII | 4 |
| PstI | 9 |
| SalI | 1 |
| SmaI | 8 |
| BglII/EcoRI | 8 |
| BglII/HindIII | 10 |
| BglII/PstI | 12 |
| BglII/SalI | 6 |
| BglII/SmaI | 11 |
| Plasmid MC5 | |
| BamHI | 3 |
| BglII | 7 |
| EcoRI | 7 |
| PstI | 5 |
| HindIII | 4 |

| Restriction Data of Plasmid 4:46 | |
|---|---|
| Restriction Enzyme | Fragment sizes (kb) |
| BglII | 20.00, 16.60, 8.70, 7.60, 5.90, 1.20 |
| ClaI | 21.00, 13.40, 6.75, 3.45 |
| EcoRI | 21.55, 12.40, 6.15, 5.50, 3.20, 1.55, 1.45 |
| HindIII | 21.00, 12.90, 5.35, 1.75 |
| PstI | 21.00, 5.50, 3.90, 3.20, 2.55, 1.65, 1.55, 1.30, 1.05 |
| SmaI | 18.20, 7.25, 5.50, 5.00, 4.15, 3.35, 2.70, 2.50 |
| BglII/EcoRI | 19.00, 9.35, 5.75, 5.25, 3.80, 2.30, 1.20, 0.85 |
| BglII/HindIII | 20.00, 11.40, 6.05, 4.20*, 2.70, 1.70, 1.20*, 0.85 |
| BglII/PstII | 20.00, 5.50, 3.40, 3.00*, 2.50, 2.05, 1.65*, 1.50, 1.20, 1.05 |
| BgII/SmaI | 15.80, 5.0, 4.20 3.75, 3.40, 3.20, 2.75, 2.50, 1.60*, 7.20 |

*These bands are doublets.

| Restriction Data of Plasmid pMC5 | |
|---|---|
| Restriction Enzyme | Fragment Sizes (kb) |
| EcoRI | 21.60, 12.75, 3.05, 2.80, 2.60, 1.20, 0.85 |
| BglII | 19.60, 8.90, 8.00, 3.60, 1.95, 1.65, 1.15 |

Hybridisation of Plasmid pMC5

Plasmid pMC5 contains sequences homologous to R. elguminosarum dct region. The region of homology has been localised to a 8.9 kb BglII fragment.

TRANSFER OF PLASMID 4.46 TO R. MELILOTI CM2

The procedure used was essentially similar to that described for the complementation experiments except that the donor strain was E. coil HB101 (4:46), the mobilizing strain was E. coli HB101 (pRK2013) and the recipient strain was R. meliloti CM2.

TRANSFER OF PLASMIDS 4:46 AND MC5 TO B. JAPONICUM CJI

Depending on which plasmid was to be transferred either E. coli HB101 (4:46) or E. coli HB101 (MC5) served as the donor strain. In both cases the mobilising strain was E. coli HB101 (pRK2013) and the recipient strain was *B. japonicum* CJI. The donor strains were grown in LB medium containing 10 ug/ml tetracycline, the mobilising strain in LB medium containing 25 ug/ml kanamycin and the recipient strain in MSY medium. The mating was preformed on MSY plates for 48 h at 30° C. The mating mix was then transferred to the exconjugant selection plates. i.e. MSY plates containing 100 μg/ml spectinomycin (selecting for *B. japonicum* CJI) and 120 μg/ml tetracycline (selecting for transfer of plasmids 4:46 or MC5) and incubated at 30° C. for 7 days.

The frequency of tetracycline transfer was $8.7 \times 10^{-5}$. The vector plasmid pRK290 was also mobilized into *B. japonicum* CJI and served as a control in subsequent experiments.

*R. japonicum* CJI containing plasmid MC5 was deposited with the National Collection of Industrial Bacteria, Torry Research Station, Aberdeen. Scotland under the accession number 12295.

TRANSFER OF PLASMID pRK290:4:46 TO *R. LEGUMINOSARUM* CL100.

Plasmid p446 was transferred to *R. lequminosarum* CL100 using plasmid pRK2013 as a helper plasmid. The donor strain *E. coli* KMBL1164 (p446) was grown in LB medium containing 10 μg/ml tetracycline, the mobilising strain *E. coli* KMBL1164 (pRK2013) in LB medium containing 25 μg/ml kanamycin and the recipient strain *R. lequminosarum* CLIOO in MSY medium. The mating was performed on MSY plates for 48 h at 30° C.

The mating mix was then transferred to the selection plates. i.e. MSY plates containing 50 μg/ml streptomycin (selecting for *R. lequminosarum* CL100) and 20 μg/ml tetracycline (selecting for transfer of plasmid p446) and incubated at 30° C. for 4 days.

INCREASED TRANSPORT ACTIVITY IN *R. MELILOTI. B. JAPONICUM* AND *R. LEGUMINOSARUM* CL100

Transport Assay

Log phase cells grown in 200 ml succinate NH+ were centrifuged at 8.000 rpm for 5 minutes at 4° C., and washed twice in Rhizobium salts buffer pH 6.8. The cells were resuspended in 3 ml transport assay solution which consisted of Rhizobium salts 10 ml/l, MOPS 10.4 g/l, ammonium sulphate 1 g/l at pH 6.8. Cell suspension was starved at 30° for three hours prior to the transport assay.

In a typical assay, 1 ml of cells was added to two mls reaction mix in a sarsted tube. Reaction mix contained transport assay solution. 20 μM 'Cold' succinate, 1 μCi 'Hot' succinate. pH 6.8 (specific activity 119.7 mCi/mM). Assay mixture was vortexed prior to removal of first sample. 100 μl samples were removed in duplicate at one minute intervals for ten minutes using a micropipette (pipetman p200). Samples were filtered using 0.45 Gelman nitrocellulose filters on a millipore 3025 sampling minifold. Filtered cells were immediately washed twice with 2 ml of ice cold Rhizobium salts containing 1 mM sodium azide. Washed cells and filters were placed in scintillation vials containing 6 ml of scintillation fluid. Vials were vortexed well and read on a Backman LS 7,000 scintillation counter for 10 minutes using program 3. Background counts were obtained by reading vials containing just scintillation fluid for 1 minute on program 3.

Non specific binding of $^{14}C$-labeled substrate to the bacterial cells was determined by using toluene-treated cells (2%) in a capped sarsted, mixing vigorously and placing in a shaking incubator for 30 minutes at 30° C. before assay.

Figure 5:
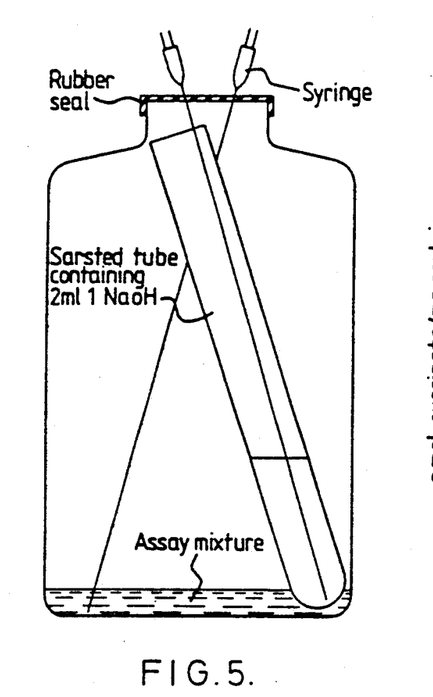
FIG. 5 shows the $CO_2$ trap used in the succinate metabolism assay.

Assay for release of $^{14}CO_2$ from assay mixture was carried out using the $CO_2$ 'trap' illustrated in FIG. 5. 100 μl samples were assayed in duplicate at time 1, 5, 10, 20, 40, 80 minutes. Samples were added directly to scintillation fluid. vortexed and counted for 10 minutes on program 3.

Protein Assay

Protein concentrations were determined by the method of Lowry et al. (1951) J.Biol.Chem. 193 (266-275).

Reagents:
1) 3% $Na_2 CO_3$ in 0.1 N NaOH
2) Alkaline Copper Reagent:
   2 ml of 2% $CuSO_4$ 5 $H_2O$ and 2 ml of 4% sodium tartarate made up to 100 ml in a volumeric flask using reagent 1.
3) Folin Ciocalteau Reagent:
   1 part was diluted with two parts water just before use and protected from light with aluminium foil.
4) Standards:
   Crystalline bovine serum albumin at 0, 30, 60, 90, 120, 150 g ml$^{-1}$ made up in same solvent as sample being assayed.

Procedure

To a sample or standard containing 10–200 μg protein in 0.5 ml in a test tube, 5 ml alkaline copper reagent was added, mixed well and allowed to stand at room temperature for at least 10 minutes, 0.5 ml diluted Folin-Ciocalteau reagent was added very rapidly and mixed within a second or two in a vortex. The mixture was allowed to stand for 30 minutes and extinction at 655 nm (E655) was measured. A standard curve relating E655 to mg protein per assay tube was drawn and the protein content of the unknown sample was estimated as mg protein assayed. Whole cells were solubilized by boiling at 80° C. for 2–3 hours in 25 mls of 0.3 N NaOH prior to assay.

Figure 6:
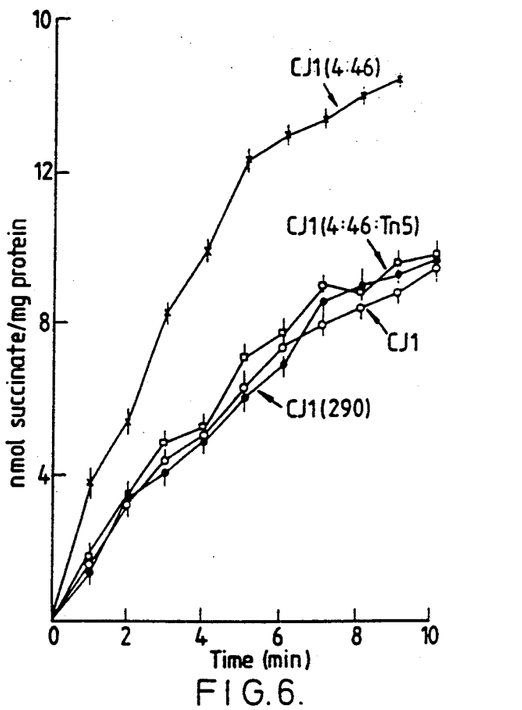
FIG. 6 is a graph showing succinate uptake by the R. japonicum strains CJI, CJI (MC5), CJI (4:46) and CJI (4:46:Tn5).

Succinate uptake was expressed as nmoles of succinate/mg protein and plotted against time. Results for *R. meliloti* strains are shown in Table 4 and results for *B. japonicum* strains are shown in FIG. 6.

TABLE 4

| Succinate Uptake (nmoles succinate/mg protein) | | |
|---|---|---|
| Time (mins) | CM2 | CM2(pRK 290:4:46) |
| 0 | 0.0 | 0.0 |
| 1 | 6.0 | 10.0 |
| 2 | 12.0 | 19.0 |
| 3 | 18.0 | 27.0 |
| 4 | 24.0 | 35.0 |
| 5 | 30.0 | 42.0 |
| 6 | 32.0 | 49.0 |
| 7 | 35.0 | 57.0 |
| 8 | 42.0 | 66.0 |
| 9 | 45.0 | 75.0 |
| 10 | 48.0 | 79.0 |

Table 4 shows succinate uptake by both the wild-type *R. meliloti* CM2 strain and the *R. meliloti* CM2 (4:46) strain.

The succinate uptake rate of *B. japonicum* CJ1 (pRK290:4:46) was compared with that of *B. jaoonicum* CJI during growth on succinate NH+ minimal medium. A time course study (FIG. 6) revealed that the uptake of $^{14}C$-labelled succinate was about two fold higher in the strain containing plasmid pRK290:4:46 (2.8 nmol/mg protein.min) compared to *B. japonicum* CJI (1.4 nmol/mg protein.min). In both strains the pattern of uptake was similar and linear for approximately the first seven minutes. When a Tn5 containing derivative of pRK290:4:46 unable to complement the *R. meliloti* Dct- strain CM12 was mobilised into *B. jaoonicum* CJ1, no increase in succinate uptake activity was observed in the resultant strain compared to *B. jaoonicum* CJI (FIG. 6). These studies indicate that the enhanced succinate uptake activity exhibited by *B. jaoonicum* CJI (pRK290:4:46) is a consequence of the expression of the introduced *R. meliloti* gene(s) in *B. japonicum*. In addition, it would appear that the same locus is responsible for both the Dct complementing phenotype and the increased succinate uptake activity.

Regulation of succinate uptake in *B. japonicum* strain CJI (pRK290:4:46)

Since the introduced *R. meliloti* gene(s) could be expressed in *B. japonicum*, the regulation of these genes was next investigated in the new background. The strains *B. japonicum* CJI and CJI (pRK290:4:46) were grown in minimal media containing a variety of different carbon sources and the specific growth rates determined (Table 5). An increase in the specific growth rate of *B. japonicum* CJ1 (pRK290:4:46) compared to that of strain CJI was only observed during growth on dicarboxylic acids (fumarate, malate or succinate). No significant difference was evident in the specific growth rates on other carbon sources. These results indicate that plasmid pRK290:4:46 specifically affects the utilisation of dicarboxylic acids.

The pattern of inhibition of succinate transport by metabolic inhibitors in the hybrid strain CJI (pRK290:4:46) was investigated and found not to differ from that in the wild type strain CJI. Sodium azide or sodium cyanide at a concentration of 10 uM inhibited succinate uptake activities by over 80% in both strains.

TABLE 5

Growth characteristics of dct modified *B. japonicum* strains under aerobic conditions[a]

| Carbon | Specific growth rate (h$^{-1}$) | | |
|---|---|---|---|
| Source | CJ1 | CJ(pRK290) | CJ(pRK290:4:46) |
| Succinate | 0.072 | 0.069 | 0.103 |
| Fumerate | 0.070 | 0.066 | 0.091 |
| Malate | 0.070 | 0.064 | 0.092 |
| Gluconate | 0.052 | 0.050 | 0.054 |
| Arabinose | 0.050 | 0.047 | 0.051 |
| Pyruvate | 0.050 | 0.050 | 0.049 |
| Glutamate | 0.049 | 0.046 | 0.049 |
| Mannitol | 0.043 | 0.039 | 0.041 |
| Glucose | 0.035 | 0.033 | 0.036 |

[a]The cultures were grown aerobically as described in the test. The nitrogen source in all cases was $(NH_4)_2SO_2$ (0.1% w/v).

An examination of the succinate uptake activities of the hybrid *B. japonicum* strains on minimal media containing various carbon sources showed that the highest rates of succinate uptake were obtained in cells grown on dicarboxylic acids (Table 6). This was similar to the pattern of succinate uptake exhibited by the wild type strain. Growth on other carbon compounds resulted in lower succinate uptake rates. clearly demonstrating that dicarboxylic acids are necessary for inducing maximum expression of the Dct system in both the wild type and modified strains. An investigation of the regulation of the Dct system by other carbon sources showed that glutamate. mannitol and arabinose did not significantly affect the transport rate in either strain CJ1 and CJ1 (pRK290:4:46) (Table 6). *B. japonicum* strain CJ1 containing the Tn5 derivative of plasmid pRK290:4:46 behaved very similarly to the parent strain CJI with respect to its succinate uptake capabilities (Table 6). These results demonstrate clearly that the expression of the *R. meliloti* gene(s) present on plasmid pRK290:4:46 results in a two-fold increase in the succinate uptake activity of the modified strain. Furthermore, this transport modification in the strain does not appear to affect the regulation of succinate uptake by either metabolic inhibitors or other carbon sources compared to the wild type strain.

TABLE 6

Regulation of succinate uptake activity in dct modified *B. japonicum* strains under aerobic conditions

| Carbon | Succinate uptake activity (nmol/mg protein · min)[a] | | |
|---|---|---|---|
| Source | CJ1 | CJ1(pRK290:4:46) | CJ1pRK290:4:46:TN = n5) |
| Succinate | 1.43 ± 0.21(100)[b] | 2.82 ± 0.14(100) | 1.39 ± 0.18(100) |
| Fumerate | 1.33 ± 0.26(93) | 2.62 ± 0.11(93) | —[c] |
| Malate | 1.31 ± 0.24(92) | 2.68 ± 0.13(95) | 1.36 ± 0.14(98) |
| Gluconate | 0.54 ± 0.18(38) | 1.02 ± 0.18(36) | 0.62 ± 0.17(45) |
| Pyruvate | 0.50 ± 0.10(35) | 0.96 ± 0.09(34) | — |
| Glutamate | 0.56 ± 0.17(39) | 1.16 ± 0.14(41) | 0.58 ± 0.09(42) |
| Mannitol | 0.49 ± 0.11(34) | 0.79 ± 0.19(28) | — |
| Arabinose | 0.46 ± 0.10(32) | 0.95 ± 0.18(34) | 0.41 ± 0.08(30) |
| Ribose | 0.43 ± 0.13(30) | 0.90 ± 0.04(32) | — |
| Succinate + Arabinose | 1.28 ± 0.24(90) | 2.71 ± 0.19(96) | 1.32 ± 0.18(95) |
| Succinate + glutamate | 1.36 ± 0.21(96) | 2.76 ± 0.16(98) | 1.28 ± 0.19(92) |
| Succinate + mannitol | 1.35 ± 0.23(95) | 2.76 ± 0.08(98) | 1.25 ± 0.14(90) |

[a]The cultures were grown aerobically as described in the test. The nitrogen source in all cases was $(NH_4)_2SO_2$ (0.1% w/v). Succinate uptake activity was determined using $^{14}C$-labelled succinate as described in the text.
[b]Each value is the mean of three replicates and is associated with its SE. The percentages of succinate uptake relative to the rates obtained by cells when grown on succinate alone are shown in parenthesis.
[c]activity not determined.

Succinate Uptake in R. lequminosarum CL100 (p446)

As shown in Table 7 succinate uptake activity was significantly higher in the R. leguminosarum CL100 strain carrying the plasmid pRK290:4:46 than in the same strain carrying the pRK290 plasmid or carrying no plasmid at all.

TABLE 7

Increase in Succinate Uptake Activity of R. leguminosarum CL100 by plasmid p 446

| Strain | Succinate uptake (nmol/min/mg protein) |
|---|---|
| R. leguminosarum CL100 | 26.2 |
| R. leguminosarum CL100 (pRK290) | 19.4 |
| R. leguminosarum CL100 (pRK290:4:46) | 38.2 |

NITROGEN FIXATION IN R. MELILOTI CARRYING PLASMID pRK 290:4:46

R. meliloti 41 and its derivatives were tested for their symbiotic properties on alfalfa. Nitrogen fixation rates were measured as described above and the results are shown in Table 8. An uninoculated control and R. meliloti CM12 which has a dct- phenotype did not fix nitrogen. R. meliloti strains carrying the pRK290:4:46 plasmid fixed more than twice as much nitrogen as the wild-type R. meliloti strain, indicating that an increase in the copy number of dct genes leads to an increase in nitrogen fixation.

TABLE 8

Increase in Nitrogen Fixation Rates by Gene Dosage effect with plasmid pRK290:4:46

| Strain | Phenotype | Nitrogen Fixation* (n moles ethylene/hr/plant) |
|---|---|---|
| R. meliloti CM2 | Dct+ | 230 |
| R. meliloti CM2(4:46) | Dct+ | 528 |
| R. meliloti CM12(4:46) | Dct+ | 621 |
| R. meliloti CM12 | Dct− | 0 |
| Uninoculated control | — | 0 |

*Activities were determined 4 weeks following germination and inoculation of alfalfa seedlings.

Free-living Nitrogenase Activity of B. japonicium strain CJ1 (pRK290:4:46)

Nitrogenase activity was determined in cell suspensions of B. japonicium by the acetylene reduction technique described by O'Gara and Shanmugan (Biochem. Biophys. Acta. 437 313-327, (1977)). Cultures were grown in minimal salts media containing 0.4% (w/v) malate and 0.1% (w/v) glutamate and an oxygen concentration of 0.76 mm Hg (standard nitrogenase induction condition), unless otherwise stated.

Figure 7:
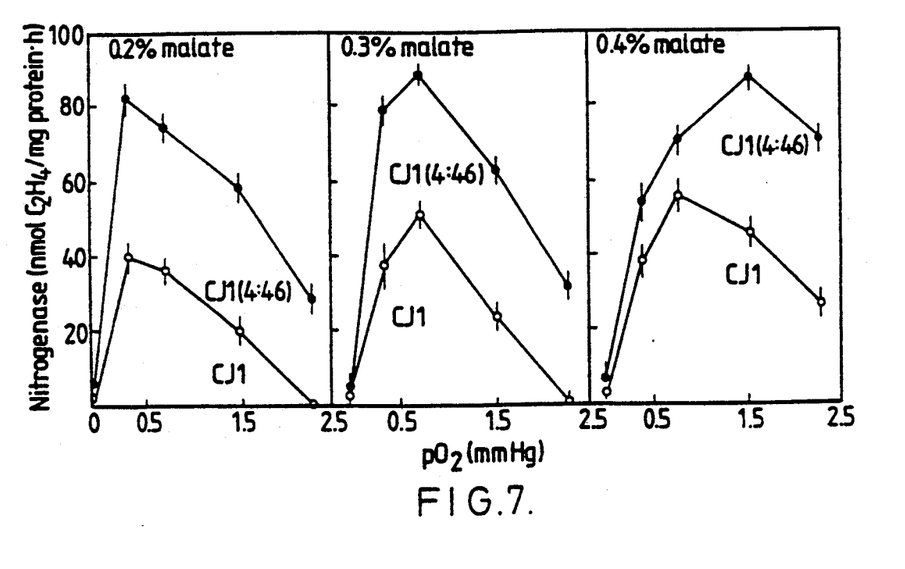
FIG. 7 shows nitrogenase activity as a function of malate and oxygen concentrations for the B. japonicum wild type strain CJI and the strain CJI )pRK290:4:46).

Having established that the presence of plasmid pRK290:4:46 in B. japonicum CJI results in an increased succinate uptake capability, the possible effect on this enhanced uptake activity on free-living nitrogenase activity under different growth conditions was next investigated. The concentrations of the dicarboxylic acid (0.2% to 0.4% w/v malate) and oxygen (0.38 to 1.52 mm Hg) provided during the nitrogenase induction assay were varied. Under all conditions tested, B. japonicum CJI (pRK290:4:46) exhibited higher acetylene reduction activities over the strain without plasmid pRK290:46 (FIG. 7). In some instances (e.g. 0.4% malate and 1.52 mm Hg $pO_2$ or 0.2% malate and 0.76 mm Hg $pO_2$) the increase was as high as 90%. The maximum level of nitrogenas activity induced by strain CJ1 (pRK:290:4:46) was 60% higher than the maximum level induced by strain CJ1. It was also observed that strain CJ1 (pRK290:4:46) exhibited maximum levels of nitrogenas at a higher oxygen concentration than strain CJ1 (1.52 mm Hg $pO_2$ as opposed to 0.76 mm $pO_2$).

The succinate uptake activities of the two strains under free-living nitrogen fixing conditions were determined to see if any correlation existed between succinate uptake and nitrogenase activities. The results obtained indicate that, for both strains, maximal succinate uptake and nitrogenase activities were obtained under the same conditions (Table 9). These results suggest that the enhanced nitrogenase activity found in strain CJ1 (pRK290:4:46) is linked to the increased uptake activity associated with this strain.

TABLE 9

Succinate uptake and nitrogenase activities in B. japonicum cultures under free-living microaerobic conditions.

| Strain | Malate Conc. (w/v)$^a$ | Succinate Uptake Act. (nmol/mg prot · min)$^d$ | Nitrogenase Act. (nmol/mg prot · h)$^c$ |
|---|---|---|---|
| CJ1 | 0.2% | 1.29 ± 0.08 | 38.2 ± 3.1 |
| CJ1(4:46) | | 2.59 ± 0.4 | 74.1 ± 2.9 |
| CJ1 | 0.3% | 1.09 ± 0.15 | 51.1 ± 2.1 |
| CJ1(4:46) | | 2.86 ± 0.3 | 88.1 ± 1.7 |
| CJ1 | 0.4% | 1.46 ± 0.1 | 54.7 ± 4.6 |
| CJ1(:4:46) | | 1.52 ± 0.16 | 71.2 ± 4.1 |
| CJ1 | 0.4%$^b$ | 1.48 ± 0.2 | 47.2 ± 2.1 |
| CJ1(4:46) | | 2.98 ± 0.7 | 88.6 ± 3.2 |

$^a$The cultures were grown under microaerophilic conditions as described in the text with glutamate (0.1% w/v) as the nitrogen source, varying concentrations of malate as the carbon source and an oxygen concentration of 0.76 mm Hg.
$^b$The cultures were grown in malate (0.4% w/v), glutamate (0.1% w/v) and an oxygen concentration of 1.52 mm Hg.
$^c$The cell yield (mg protein/ml) of the cultures was determined 150 h after inoculation.
$^d$Succinate uptake was measured approximately 50 h after inoculation.

Each value is the mean of at least three replicates and is associated with its SE.

The present invention has an obvious industrial application in increasing nitrogen fixation in leguminous plants. The bacterial host may carry the additional DNA fragment encoding the dct genes itself or it may harbour a plasmid carrying such a DNA fragment. The bacterial strain R. meloliti is suitable for use with alfalfa crops, B. japonicum can be used with soya bean crops and R. leguminosarum can be used with pea crops. The DNA inserts encoding the dct genes may be transferred to other strains of bacteria which fix nitrogen. It would be particularly advantageous for such genes to be modified by coupling to a promoter sequence which would lead to even further enhancement of expression.

I claim:
1. An isolated fragment of DNA selected from:
   (i) DNA in plasmid pRK290:4:46, deposited under accession number 12294 at the National Collection of Industrial Bacteria, Torry Research Station, Aberdeen, Scotland, capable of conferring an increased nitrogen fixing ability of Rhizobium species into which it is transferred, the Rhizobium species initially having a DCT+ phenotype and an ability to fix nitrogen, and
   (ii) DNA of sufficient sequence identity with the DNA of (i) to confer the increase in nitrogen-fixing ability.
2. A fragment of DNA isolated from R. meliloti encoding genese which complement dicarboxylic acid transport mutant Rhizobium meliloti CM12 as deposited under the accession No. 12294 at the National Collec- tion of Industrial Bacteria, Torry Research Station, Aberdeen, Scotland, wherein said fragment of DNa is capable of conferring an increase in nitrogen-fixing ability on Rhizobium species into which it is transferred, the Rhizobium species initially having a DCT+ phenotype and an ability to fix nitrogen.

3. An isolated fragment of DNA selected from:
(i) DNA is plasmid pRK290:4:46, deposited under accession number 12294 at the National Collection of Industrial Bacteria, Torry Research Station, Aberdeen, Scotland, capable of conferring an increase in nitrogen-fixing ability on Rhizobium species into which it is transferred, the Rhizobium species initially having a DCT+ phenotype and an ability to fix nitrogen, and
(ii) DNA of sufficient sequence identity with the DNA of (i) to complement dicarboxylic acid transport mutant *Rhizobium meliloti* CM12 as deposited under accession No. 12294, and to confer the increase in nitrogen-fixation.

4. A fragment of DNA as claimed in claim 1 having the restriction data:

| Restriction Enzyme | Fragment Sizes (kb) |
| --- | --- |
| EcoRI | 21.55, 12.40, 6.15, 5.50, 3.20, 1.55, 1.45 |
| SmaI | 18.20, 7.25, 5.50, 5.00, 4.15, 3.35, 2.70, 2.50 |
| BglII/EcoRI | 19.00, 9.35, 5.75, 5.25, 3.80, 2.30, 1.20, 0.85. |

5. A fragment of DNA as claimed in claim 1 which confers increased nitrogen fixing ability on plants infected/inoculated with Rhizobium species into which the said DNA fragment is transferred.

6. A fragment of DNA as claimed in claim 1 having the restriction data:

| Restriction Enzyme | No. of Fragments |
| --- | --- |
| BglII | 6 |
| ClaI | 4 |
| EcoRI | 7 |
| HindIII | 4 |
| PstI | 9 |
| SalI | 1 |
| SmaI | 8 |
| BglII/EcoRI | 8 |
| BglII/HindIII | 10 |
| BglII/PstI | 12 |
| BglII/SalI | 6 |
| BglII/SmaI | 11. |

7. A plasmid conveying a DNA fragment as claimed in claim 1.

8. A plasmid according to claim 7 which is pRK290:4:46 deposited with the National Collection of Industrial Bacteria, Torry Research Station, Aberdeen, Scotland under the accession number NCIB 12294.

9. Bacterial hosts containing a fragment of DNA as claimed in claim 1.

10. Bacterial hosts containing a plasmid as claimed in claim 7.

11. Bacterial hosts as claimed in claim 9 selected from *R. meliloti, B. japonicum*, and *R. leguminosarum*.

12. Bacterial hosts as claimed in claim 10 selected from *R. meliloti, B. japonicum*, and *R. leguminosarum*.

13. A method of increasing dicarboxylic acid transport in Rhizobium species comprising transferring into the said species a fragment of DNa as claimed in claim 1.

* * * * *